(12) United States Patent
Mazmanian et al.

(10) Patent No.: US 9,057,070 B2
(45) Date of Patent: Jun. 16, 2015

(54) **GENERATION OF *BACTERIODES FRAGILIS* CAPSULAR POLYSACCHARIDE A-ONLY PRODUCING MUTANT STRAIN**

(71) Applicants: California Institute of Technology, Pasadena, CA (US); The Brigham and Women's Hospital, Inc., Boston, MA (US)

(72) Inventors: Sarkis K. Mazmanian, Porter Ranch, CA (US); Sung-Eun Lee, Los Angeles, CA (US); Dennis L. Kasper, Charlestown, MA (US)

(73) Assignees: California Institute of Technology, Pasadena, CA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/573,695

(22) Filed: Oct. 3, 2012

(65) Prior Publication Data

US 2013/0121966 A1 May 16, 2013

Related U.S. Application Data

(60) Provisional application No. 61/542,549, filed on Oct. 3, 2011.

(51) Int. Cl.
| | | |
|---|---|---|
| *C12N 1/12* | (2006.01) | |
| *C12N 1/20* | (2006.01) | |
| *C12P 21/06* | (2006.01) | |
| *C12P 19/04* | (2006.01) | |
| *C12N 15/74* | (2006.01) | |
| *A61K 35/74* | (2015.01) | |

(52) U.S. Cl.
CPC .............. *C12N 15/74* (2013.01); *A61K 35/74* (2013.01); *C12P 19/04* (2013.01); *C12N 1/20* (2013.01)

(58) Field of Classification Search
CPC .......... C12N 15/74; C12N 1/20; C61K 35/74; C12P 19/04
USPC ............................ 435/252.1, 252.3, 69.1, 101
See application file for complete search history.

(56) References Cited

U.S. PATENT DOCUMENTS

| 5,679,654 A | 10/1997 | Tzianabos et al. |
| 2004/0219160 A1 | 11/2004 | Tzianabos et al. |
| 2008/0057565 A1 | 3/2008 | Comstock et al. |
| 2009/0124573 A1 | 5/2009 | Mazmanian et al. |
| 2010/0275282 A1 | 10/2010 | Round et al. |
| 2011/0251156 A1 | 10/2011 | Shen et al. |
| 2011/0287048 A1 | 11/2011 | Round et al. |
| 2012/0087895 A1 | 4/2012 | Mazmanian et al. |
| 2013/0064859 A1 | 3/2013 | Mazmanian et al. |

OTHER PUBLICATIONS

Mazmanian SK, et al., Nature. May 29, 2008;453(7195):620-5. doi: 10.1038/nature07008. A microbial symbiosis factor prevents intestinal inflammatory disease.*
Nakayama-Imaohji H et al, J Bacteriol. Oct. 2009;191(19):6003-11. doi: 10.1128/JB.00687-09. Epub Jul. 31, 2009. Identification of the site-specific DNA invertase responsible for the phase variation of SusC/SusD family outer membrane proteins in *Bacteroides fragilis*.*
Patrict et al Mutational analysis of genes implicated in LPS and capsular polysaccharide biosynthesis in the opportunistic pathogen *Bacteroides fragilis* Microbiology. Apr. 2009;155(Pt 4):1039-49.*
Troy et al., Beneficial effects of *Bacteroides fragilis* polysaccharides on the immune system ; 2010 Front Biosci. ; 15: 25-34.*
Ochoa-Repáraz et al., A polysaccharide from the human commensal *Bacteroides fragilis* protects against CNS demyelinating disease Mucosal Immunology (2010) 3, 487-495.*
Coyne, Michael J. et al., "Mpi recombinase globally modulates the surface architecture of a human commensal bacterium". PNAS, Sep. 2, 2003, vol. 100, No. 18, p. 10446-10451.
Troy, Erin B. et al., "Orientations of the *Bacteroides fragilis* capsular polysaccharide biosynthesis locus promoters during symbiosis and infection", Journal of Bacteriology, Nov. 2010, vol. 192, No. 21, pp. 5832-5836.
Coyne, Michael J. et al, "*Bacteroides fragilis* NCTC9343 Produces at Least Three Distinct Capsular Polysaccharides: Cloning, Characterization, and Reassignment of Polysaccharide B and C Biosynthesis Loci", Infection and Immunity, Nov. 2000, p. 6176-6181.
Liu, Cui Hua, et al., "Regulation of surface architecture by symbiotic bacteria mediates host colonization", PNAS, Mar. 11, 2008, vol. 105, No. 10, pp. 3951-3956.
Round, J.L., et al., Inducible Foxp3+ Regulatory T-Cell development by a Commensal Bacterium of the Intestinal Microbiota, Proc. Natl. Acad. Sci (USA) 107:12204-12209 (2010).
May 30, 2013 Office Action in U.S. Appl. No. 13/112,725 of Round et al.

* cited by examiner

*Primary Examiner* — Maria Leavitt
(74) *Attorney, Agent, or Firm* — Berliner & Associates

(57) ABSTRACT

Provided is an isolated *B. fragilis* bacterial cell producing a native capsular polysaccharide A (PSA), wherein the cell is incapable of producing capsular polysaccharides PSB, PSC, PSD, PSE, PSF, PSG, and PSH because the cell's biosynthetic genes for native capsular polysaccharides PSB, PSC, PSD, PSE, PSF, PSG, and PSH have been deleted from the cell's genome. The isolated or wild type *B. fragilis* cell, or an extract obtained from said *B. fragilis* cell, can be used to treat individuals with inflammation.

5 Claims, 4 Drawing Sheets

WC- whole cell extract, OMV- outer membrane vesicles

SEQUENCE LISTING

```
<160> NUMBER OF SEQ ID NOS: 56

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
aaatgcgttg cttttgcttt                                                    20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
ttcgaaatcg ttttgcttca                                                    20

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
ccatggttta tgctggcttt                                                    20

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
aacactacgc ctacccgatg                                                    20

<210> SEQ ID NO 5
<211> LENGTH: 20
```

```
<212> TYPE: DNA
<213> ORGANISM: Artificial Sequence
<220> FEATURE:
<223> OTHER INFORMATION: PCR primer

<400> SEQUENCE: 5
tactgaccga acccacatca                                              20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
cgatccgatc tgtcatagca                                              20

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
aaccggctaa aaatggaagg                                              20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
atcggcactc caacagactt                                              20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
acttacgttc aacgccatcc                                              20

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
gagattgcct gggtgaaaaa                                              20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
```

-continued gtccataagc ttgacgcaca                                              20

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
cgtgcaggta atgtgattgg                                              20

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
tttgtgagcg tttgctcaat                                              20

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
catcctccca tgcctaaaga                                              20

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
gtgcggtgct ggttttaat                                               20

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16
ctatgccaag cggaaagaag                                              20

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17
ccctattggc cggttttatt                                              20

<210> SEQ ID NO 18
<211> LENGTH: 20
<212> TYPE: DNA
<213> ORGANISM: Artificial Sequence

```
<220> FEATURE:
<223> OTHER INFORMATION: PCR primer

<400> SEQUENCE: 18
ttggctttat cgtccgtacc                                               20

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
ccacttcaac accattgacg                                               20

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
cccctctcca atatcagcaa                                               20

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
attcccgcaa gtgcagatag                                               20

<210> SEQ ID NO 22
<211> LENGTH: 20
<212> TYPE: DNA
<213> ORGANISM: Artificial Sequence
<220> FEATURE:
<223> OTHER INFORMATION: PCR primer

<400> SEQUENCE: 22
tttaagcgac gtggaggttt                                               20

<210> SEQ ID NO 23
<211> LENGTH: 20
<212> TYPE: DNA
<213> ORGANISM: Artificial Sequence
<220> FEATURE:
<223> OTHER INFORMATION: PCR primer

<400> SEQUENCE: 23
tcagtcccac ccacacagta                                               20

<210> SEQ ID NO 24
<211> LENGTH: 20
<212> TYPE: DNA
<213> ORGANISM: Artificial Sequence
<220> FEATURE:
<223> OTHER INFORMATION: PCR primer

<400> SEQUENCE: 24
cacttacagc cgtgagcttg                                               20
```

<210> SEQ ID NO 25
<211> LENGTH: 20
<212> TYPE: DNA
<213> ORGANISM: Artificial Sequence
<220> FEATURE:
<223> OTHER INFORMATION: PCR primer

<400> SEQUENCE: 25
gcgcaagctt ctggtttaag                                          20

<210> SEQ ID NO 26
<211> LENGTH: 20
<212> TYPE: DNA
<213> ORGANISM: Artificial Sequence
<220> FEATURE:
<223> OTHER INFORMATION: PCR primer

<400> SEQUENCE: 26
ctccaaagcc ttcactttcg                                          20

<210> SEQ ID NO 27
<211> LENGTH: 20
<212> TYPE: DNA
<213> ORGANISM: Artificial Sequence
<220> FEATURE:
<223> OTHER INFORMATION: PCR primer

<400> SEQUENCE: 27
gctaagaccg ttgccaaaat                                          20

<210> SEQ ID NO 28
<211> LENGTH: 20
<212> TYPE: DNA
<213> ORGANISM: Artificial Sequence
<220> FEATURE:
<223> OTHER INFORMATION: PCR primer

<400> SEQUENCE: 28
acccgcaaaa cagaaatgac                                          20

<210> SEQ ID NO 29
<211> LENGTH: 20
<212> TYPE: DNA
<213> ORGANISM: Artificial Sequence
<220> FEATURE:
<223> OTHER INFORMATION: PCR primer

<400> SEQUENCE: 29
aaatgcgttg cttttgcttt                                          20

<210> SEQ ID NO 30
<211> LENGTH: 20
<212> TYPE: DNA
<213> ORGANISM: Artificial Sequence
<220> FEATURE:
<223> OTHER INFORMATION: PCR primer

<400> SEQUENCE: 30
ttcgaaatcg ttttgcttca                                          20

<210> SEQ ID NO 31
<211> LENGTH: 20
<212> TYPE: DNA
<213> ORGANISM: Artificial Sequence
<220> FEATURE:
<223> OTHER INFORMATION: PCR primer -continued

```
<400> SEQUENCE: 31
catggagaaa acatcgttgg                                               20

<210> SEQ ID NO 32
<211> LENGTH: 20
<212> TYPE: DNA
<213> ORGANISM: Artificial Sequence
<220> FEATURE:
<223> OTHER INFORMATION: PCR primer

<400> SEQUENCE: 32
cccaatatcg ttcagccaaa                                               20

<210> SEQ ID NO 33
<211> LENGTH: 21
<212> TYPE: DNA
<213> ORGANISM: Artificial Sequence
<220> FEATURE:
<223> OTHER INFORMATION: PCR primer

<400> SEQUENCE: 33
ggaggatgtt tgaattggtg g                                             21

<210> SEQ ID NO 34
<211> LENGTH: 20
<212> TYPE: DNA
<213> ORGANISM: Artificial Sequence
<220> FEATURE:
<223> OTHER INFORMATION: PCR primer

<400> SEQUENCE: 34
cccgcttaat gccctaaaat                                               20

<210> SEQ ID NO 35
<211> LENGTH: 21
<212> TYPE: DNA
<213> ORGANISM: Artificial Sequence
<220> FEATURE:
<223> OTHER INFORMATION: PCR primer

<400> SEQUENCE: 35
ggaggatgtt tgaattggtg g                                             21

<210> SEQ ID NO 36
<211> LENGTH: 23
<212> TYPE: DNA
<213> ORGANISM: Artificial Sequence
<220> FEATURE:
<223> OTHER INFORMATION: PCR primer

<400> SEQUENCE: 36
tatcctgatg ttctgctttt ccg                                           23

<210> SEQ ID NO 37
<211> LENGTH: 20
<212> TYPE: DNA
<213> ORGANISM: Artificial Sequence
<220> FEATURE:
<223> OTHER INFORMATION: PCR primer

<400> SEQUENCE: 37
gtatcccgac gttacgagga                                               20

<210> SEQ ID NO 38
```

```
<211> LENGTH: 20
<212> TYPE: DNA
<213> ORGANISM: Artificial Sequence
<220> FEATURE:
<223> OTHER INFORMATION: PCR primer

<400> SEQUENCE: 38
cgaggaatct tggcattgat                                                    20

<210> SEQ ID NO 39
<211> LENGTH: 20
<212> TYPE: DNA
<213> ORGANISM: Artificial Sequence
<220> FEATURE:
<223> OTHER INFORMATION: PCR primer

<400> SEQUENCE: 39
gtatcccgac gttacgagga                                                    20

<210> SEQ ID NO 40
<211> LENGTH: 20
<212> TYPE: DNA
<213> ORGANISM: Artificial Sequence
<220> FEATURE:
<223> OTHER INFORMATION: PCR primer

<400> SEQUENCE: 40
ccatttggat aggcgagaaa                                                    20

<210> SEQ ID NO 41
<211> LENGTH: 20
<212> TYPE: DNA
<213> ORGANISM: Artificial Sequence
<220> FEATURE:
<223> OTHER INFORMATION: PCR primer

<400> SEQUENCE: 41
ctgaaagcgc attttcaaca                                                    20

<210> SEQ ID NO 42
<211> LENGTH: 20
<212> TYPE: DNA
<213> ORGANISM: Artificial Sequence
<220> FEATURE:
<223> OTHER INFORMATION: PCR primer

<400> SEQUENCE: 42
tgcatttcat ggaggaacaa                                                    20

<210> SEQ ID NO 43
<211> LENGTH: 20
<212> TYPE: DNA
<213> ORGANISM: Artificial Sequence
<220> FEATURE:
<223> OTHER INFORMATION: PCR primer

<400> SEQUENCE: 43
ttgatgggga atgaatggtt                                                    20

<210> SEQ ID NO 44
<211> LENGTH: 20
<212> TYPE: DNA
<213> ORGANISM: Artificial Sequence
<220> FEATURE:
<223> OTHER INFORMATION: PCR primer

<400> SEQUENCE: 44
```
tgcatttcat ggaggaacaa                                           20

<210> SEQ ID NO 45
<211> LENGTH: 20
<212> TYPE: DNA
<213> ORGANISM: Artificial Sequence
<220> FEATURE:
<223> OTHER INFORMATION: PCR primer

<400> SEQUENCE: 45
gcccatgtca gatttgcttt                                           20

<210> SEQ ID NO 46
<211> LENGTH: 20
<212> TYPE: DNA
<213> ORGANISM: Artificial Sequence
<220> FEATURE:
<223> OTHER INFORMATION: PCR primer

<400> SEQUENCE: 46
taggcaaaat atccggcatc                                           20

<210> SEQ ID NO 47
<211> LENGTH: 20
<212> TYPE: DNA
<213> ORGANISM: Artificial Sequence
<220> FEATURE:
<223> OTHER INFORMATION: PCR primer

<400> SEQUENCE: 47
gcccatgtca gatttgcttt                                           20

<210> SEQ ID NO 48
<211> LENGTH: 20
<212> TYPE: DNA
<213> ORGANISM: Artificial Sequence
<220> FEATURE:
<223> OTHER INFORMATION: PCR primer

<400> SEQUENCE: 48
atgaatgaag ccgaaaatcg                                           20

<210> SEQ ID NO 49
<211> LENGTH: 20
<212> TYPE: DNA
<213> ORGANISM: Artificial Sequence
<220> FEATURE:
<223> OTHER INFORMATION: PCR primer

<400> SEQUENCE: 49
aatgccggtt gttttggtta                                           20

<210> SEQ ID NO 50
<211> LENGTH: 20
<212> TYPE: DNA
<213> ORGANISM: Artificial Sequence
<220> FEATURE:
<223> OTHER INFORMATION: PCR primer

<400> SEQUENCE: 50
acagaacctg ctcccactgt                                           20

<210> SEQ ID NO 51
<211> LENGTH: 20
<212> TYPE: DNA

```
<213> ORGANISM: Artificial Sequence
<220> FEATURE:
<223> OTHER INFORMATION: PCR primer

<400> SEQUENCE: 51
aatgccggtt gttttggtta                                              20

<210> SEQ ID NO 52
<211> LENGTH: 20
<212> TYPE: DNA
<213> ORGANISM: Artificial Sequence
<220> FEATURE:
<223> OTHER INFORMATION: PCR primer

<400> SEQUENCE: 52
cggatcataa aatcggcaac                                              20

<210> SEQ ID NO 53
<211> LENGTH: 20
<212> TYPE: DNA
<213> ORGANISM: Artificial Sequence
<220> FEATURE:
<223> OTHER INFORMATION: PCR primer

<400> SEQUENCE: 53
cgggtaaaac tctgcccata                                              20

<210> SEQ ID NO 54
<211> LENGTH: 20
<212> TYPE: DNA
<213> ORGANISM: Artificial Sequence
<220> FEATURE:
<223> OTHER INFORMATION: PCR primer

<400> SEQUENCE: 54
gctcgtatgg atgctgatga                                              20

<210> SEQ ID NO 55
<211> LENGTH: 20
<212> TYPE: DNA
<213> ORGANISM: Artificial Sequence
<220> FEATURE:
<223> OTHER INFORMATION: PCR primer

<400> SEQUENCE: 55
cgggtaaaac tctgcccata                                              20

<210> SEQ ID NO 56
<211> LENGTH: 20
<212> TYPE: DNA
<213> ORGANISM: Artificial Sequence
<220> FEATURE:
<223> OTHER INFORMATION: PCR primer

<400> SEQUENCE: 56
aggtgctttc gtgattgctt                                              20
```

GENERATION OF *BACTERIODES FRAGILIS* CAPSULAR POLYSACCHARIDE A-ONLY PRODUCING MUTANT STRAIN

CROSS REFERENCE TO RELATED APPLICATIONS

This application claims the benefit of Provisional Patent Application 61/542,549 filed on Oct. 3, 2011, which is incorporated by reference herein in its entirety.

STATEMENT OF GOVERNMENT GRANT

This invention was made with government support under R21DK083633 and RO1DK078938A awarded by the National Institutes of Health. The U.S. Government has certain rights in this invention.

REFERENCE TO SEQUENCE LISTING

A Sequence Listing is submitted herewith through EFS-Web as an ASCII compliant text file. The text file is named "7920112ST25.txt", was created on Jan. 17, 2013, and is 10 kilobytes in size. The Sequence Listing is incorporated by reference herein.

FIELD OF THE INVENTION

The invention relates to treatments *B. fragilis*. More particularly this invention relates to the generation of PSA only producing mutant strains of *B. fragilis*.

BACKGROUND

*Bacteroides fragilis* produces at least 8 different capsular polysaccharides. In order to facilitate purification of PSA from the other 7 capsular polysaccharides. Others have engineered a PSA producing strain employed mutation of a regulatory gene that controls the transcription of polysaccharide production genes, but left the actual genes that are required for all capsular polysaccharide synthesis intact. However, subsequent to the creation of this strain, it was shown that secondary mutations could cause reversion to polysaccharide production (1).

SUMMARY

We created a novel bacterial strain for the production of Polysaccharide A (PSA). In order to facilitate purification of PSA from the other 7 capsular polysaccharides, we devised a strategy to mutate the genes required for production of all known polysaccharides except PSA. This was accomplished by DNA recombination (as described below) to delete the genes that encode for proteins that synthesize all non-PSA polysaccharides, ensuring that additional mutations would not restore production of other polysaccharides. The previous strategy to engineer a PSA producing strain employed mutation of a regulatory gene that controls the transcription of polysaccharide production genes, but left the actual genes that are required for all capsular polysaccharide synthesis intact.

However, subsequent to the creation of this previous strain, it was shown that secondary mutations could cause reversion to polysaccharide production (1). The current approach of deleting the genes that are required for polysaccharide production would overcome this potential shortcoming, and ensure a strain that is stable in this genotype and phenotype.

In an embodiment an isolated *B. fragilis* bacterial cell producing a native capsular polysaccharide A (PSA) is provided, wherein the cell is incapable of producing capsular polysaccharides PSB, PSC, PSD, PSE, PSF, PSG, and PSH.

In an aspect of any embodiments described herein, the cell's biosynthetic genes for native capsular polysaccharides PSB, PSC, PSD, PSE, PSF, PSG, and PSH have been deleted from the cell's genome.

In yet another aspect of any embodiments described herein, a promoter that controls expression of PSA has not been modified.

In an aspect of any embodiments described herein, the PSA promoter has one or more repeat flanking regions surrounding the promoter, and wherein said flanking regions have not been modified.

In yet another aspect of any embodiments described herein, the cell is administered, as part of a pharmaceutical, to individuals suffering from an inflammatory disease or condition.

In an aspect of any embodiments described herein a composition is provided comprising a bacterial extract or cellular fraction obtained from a *B. fragilis* bacterial cell that produces a native capsular polysaccharide A (PSA) wherein the cell is incapable of producing capsular polysaccharides PSB, PSC, PSD, PSE, PSF, PSG, and PSH, wherein the cell's biosynthetic genes for native capsular polysaccharides PSB, PSC, PSD, PSE, PSF, PSG, and PSH have been deleted from the cell's genome.

In yet another aspect of any embodiments described herein, a method to treat an individual with inflammation is provided comprising administering to said individual an effective amount of a pharmaceutical comprising an isolated *B. fragilis* bacterial cell, or an extract or cellular fraction of said cell, wherein the cell produces a native capsular polysaccharide A (PSA); and wherein the cell's biosynthetic genes for native capsular polysaccharides PSB, PSC, PSD, PSE, PSF, PSG, and PSH have been deleted from the cell's genome.

In yet another aspect of any embodiments described herein, the cellular fraction is an outer membrane vesicular fraction.

DETAILED DESCRIPTION

Figure 1:
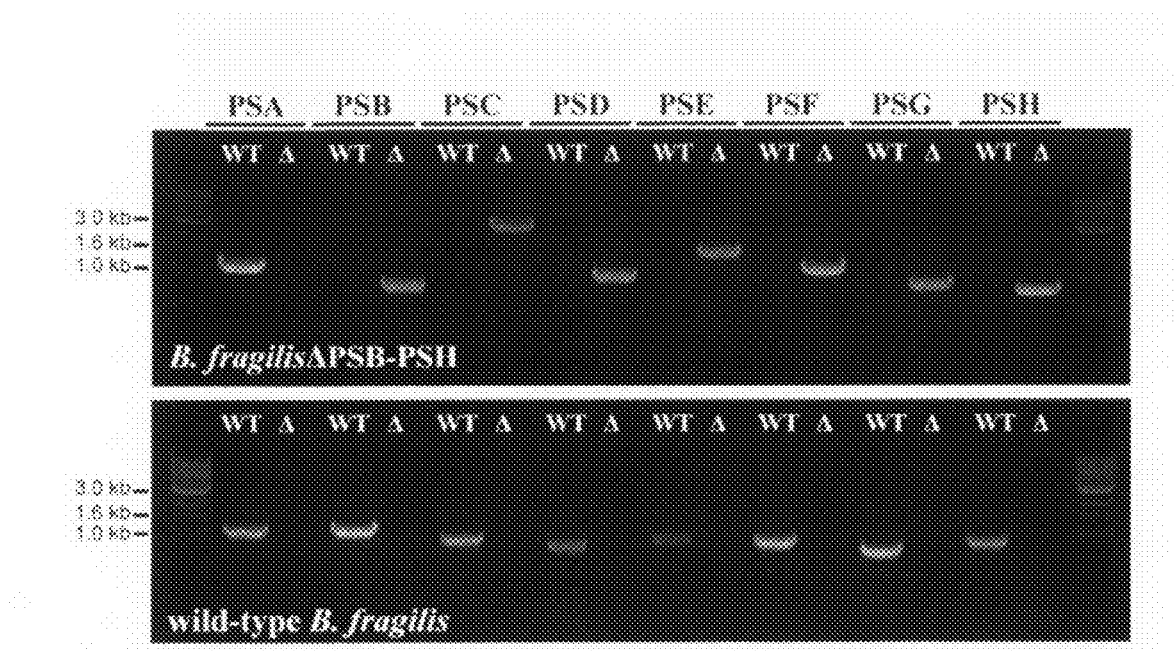
FIG. 1: Shows a gel showing the genotype of the PSA-only expressing mutant (*B. fragilis*ΔPSB-PSH) compared to the wild-type *B. fragilis* 9343 by CPS specific PCR analysis. Wild-type (WT) is distinguished from the deletion mutant (Δ) at a given locus using primers in Table 2.
Figure 2:
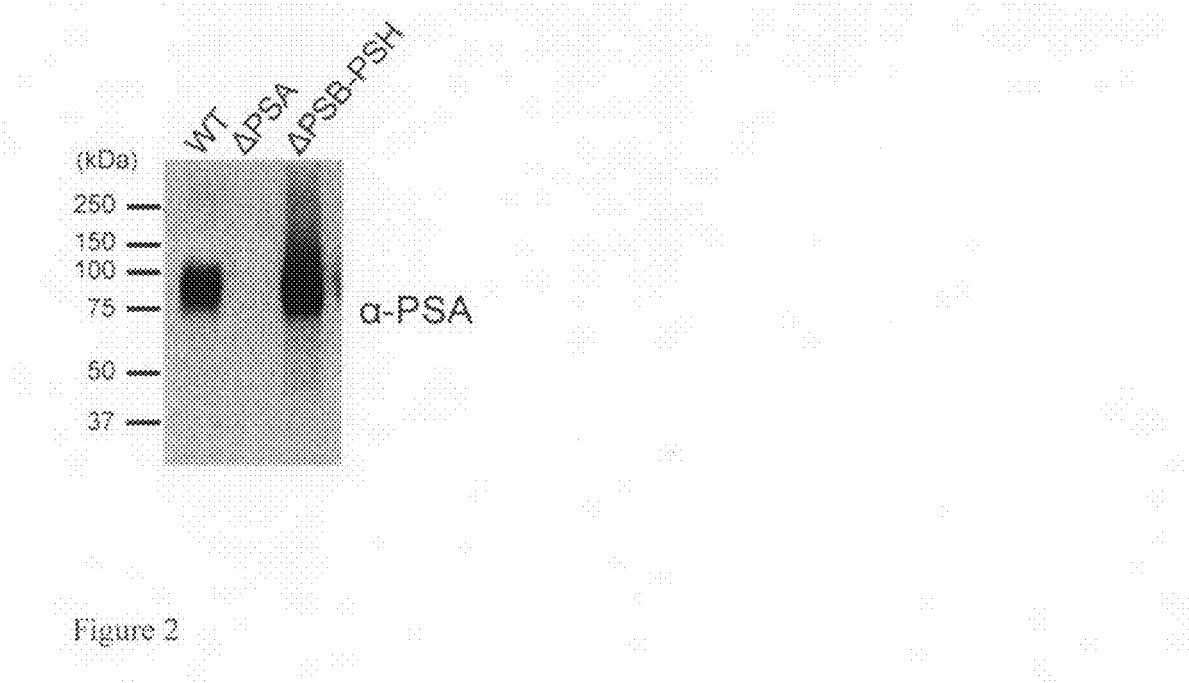
FIG. 2: Shows an immunoblot analysis confirms PSA expression by *B. fragilis*ΔPSB-PSH mutant. Rabbit anti-PSA antiserum was used at 1:1000 dilution to probe for PSA and goat anti-rabbit secondary antibody was used at 1:5000 dilution. ΔPSA refers to a strain that is deleted only in the genes required for PSA biosynthesis. The lack of reactivity for this sample shows that the antibody used is specific for PSA and not any other molecule produced by the bacteria.
Figure 3:
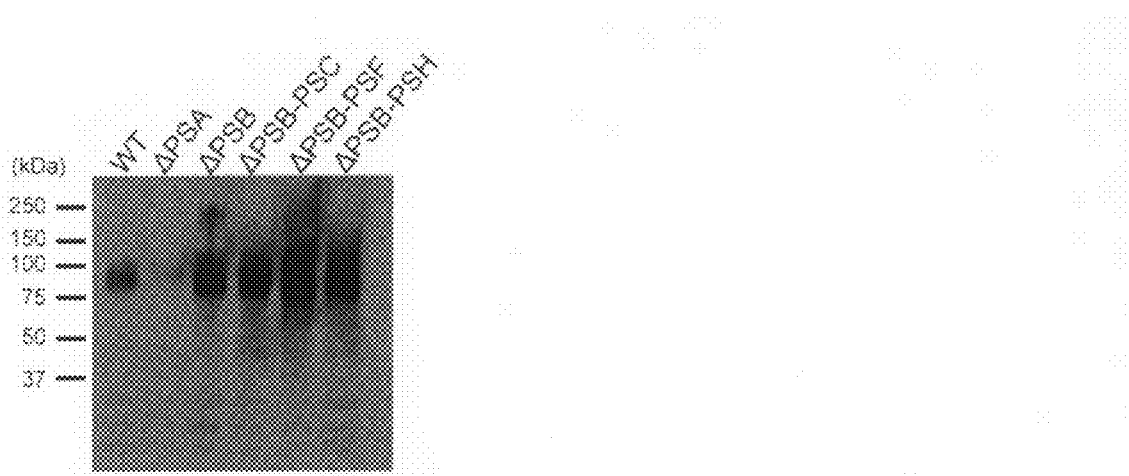
FIG. 3: Shows an immunoblot analysis confirms PSA expression by *B. fragilis* CPS mutants ΔPSA, ΔPSB, ΔPSB-PSC, ΔPSB-PSF, and ΔPSB-PSH. Rabbit anti-PSA antiserum was used at 1:3000 dilution to probe for PSA and goat anti-rabbit secondary antibody was used at 1:5000 dilution.

A "promoter controlling expression of a capsular polysaccharide" as used herein refers to a nontranscribed genetic element associated with and controlling the transcription of a capsular polysaccharide biosynthesis gene. The capsular polysaccharide biosynthesis gene can occur as part of a polycistronic capsular polysaccharide biosynthesis locus. A given promoter can regulate transcription of one or more capsular polysaccharide biosynthesis genes within the associated capsular polysaccharide biosynthesis gene locus. The promoter can include inverted repeat regions separated by intervening sequence. In one embodiment the promoter is contained between inverted repeat regions in the intervening sequence and is subject to inversion such that in one orientation the promoter is transcriptionally active ("on") with respect to the capsular polysaccharide biosynthesis gene, while in the opposite or flipped orientation the promoter is transcriptionally inactive ("off") with respect to the capsular polysaccharide biosynthesis gene.

The term "native" when used in connection with biological materials such as nucleic acid molecules, polypeptides, host cells, bacterial cells/strains and the like, refers to materials as they are found in nature and not manipulated by man.

The term "isolated" when used in connection biological materials such as nucleic acid molecules, polypeptides, bacterial cells, host cells, bacterial cells/strains and the like, refers to the isolated or purified aforementioned materials, where these materials do not occur naturally and/or where they have markedly different or distinctive characteristics compared to those found in the native material.

The wording "polysaccharide A" (or PSA, or PSA ligand) as used herein indicates a molecule produced by the PSA locus of *Bacteroides fragilis* and derivatives thereof which include but are not limited to polymers of the repeating unit {→3) α-d-AAT Galp(1→4)-[β-d-Galf(1→3)] α-d-GalpNAc(1→3)-[4,6-pyruvate]-β-d-Galp(1→}, where AATGa is acetamido-amino-2,4,6-trideoxygalactose, and the galactopyranosyl residue is modified by a pyruvate substituent spanning O-4 and O-6. The term "derivative" as used herein with reference to a first polysaccharide (e.g., PSA), indicates a second polysaccharide that is structurally related to the first polysaccharide and is derivable from the first polysaccharide by a modification that introduces a feature that is not present in the first polysaccharide while retaining functional properties of the first polysaccharide. Accordingly, a derivative polysaccharide of PSA, usually differs from the original polysaccharide by modification of the repeating units or of the saccharidic component of one or more of the repeating units that might or might not be associated with an additional function not present in the original polysaccharide. A derivative polysaccharide of PSA retains however one or more functional activities that are herein described in connection with PSA in association with the anti-inflammatory activity of PSA.

In one embodiment, low molecular weight PSA (L-PSA), as used herein, refers to PSA molecule with a molecular weight from 70 kDa to 200 kDa; and high molecular weight PSA (H-PSA), as used herein, refers to PSA molecule whose molecular weight is above 200 kDa.

In particular, in embodiments where the isolated bacterial strain/cell disclosed in this application, or OMV or PSA obtained from said strain, is used as an anti-inflammatory compound, the condition can be any condition associated to an inflammation or inflammatory response; or a condition described as an inflammatory disease itself. The wording "associated to" as used herein with reference to two items indicates a relation between the two items such that the occurrence of a first item is accompanied by the occurrence of the second item, which includes but is not limited to a cause-effect relation and sign/symptoms-disease relation.

Conditions associated with an inflammation (or inflammatory diseases) in humans include but are not limited to inflammatory bowel disease, including but not limited to Crohn's disease and ulcerative colitis, asthma, dermatitis, arthritis, myasthenia gravis, Grave's disease, multiple sclerosis (MS), type I diabetes, type 2 diabetes, food allergy, and psoriasis. A person of skill in the art would be able to identify such subjects suffering from the aforementioned diseases using the appropriate clinical criteria.

In one embodiment, compositions, extracts, or pharmaceutical composition comprising the isolated bacterial strain/cell disclosed in this application or OMVs, extracts, or PSA obtained from said strain, can be used to treat or prevent inflammatory diseases, such as, but not limited to, inflammatory bowel disease (including Crohn's disease and ulcerative colitis), asthma, dermatitis, arthritis, myasthenia gravis, Grave's disease, multiple sclerosis, and psoriasis.

The term "treatment" or "treated" as used herein indicates any activity whether part of a medical care, or not, for or deals with a condition medically or surgically in animals or humans. Such treatments can be administered by either medical or non-medical personnel.

In some embodiments, where the composition is to be administered to an individual with another compound/drug, and/or a pharmaceutically acceptable or appropriate carrier/vehicle or excipient.

The term "excipient" as used herein indicates an inactive substance used as a pharmaceutically acceptable or appropriate carrier for the active ingredients of a medication. Suitable excipients for the pharmaceutical compositions herein disclosed include any substance that enhances the ability of the body of an individual to absorb vesicles herein described. Suitable excipients also include any substance that can be used to bulk up formulations with vesicles herein described to allow for convenient and accurate dosage. In addition to their use in the single-dosage quantity, excipients can be used in the manufacturing process to aid in the handling of vesicles herein described. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

Pharmaceutically acceptable or appropriate carriers can be, but not limited to, organic or inorganic, solid or liquid excipient which is suitable for the selected mode of application such as oral application or injection, and administered in the form of a conventional pharmaceutical preparation. Such preparation includes solid such as tablets, granules, powders, capsules, and liquid such as solution, emulsion, suspension and the like. Said carrier includes starch, lactose, glucose, sucrose, dextrine, cellulose, paraffin, fatty acid glyceride, water, alcohol, gum arabic and the like. If necessary, auxiliary, stabilizer, emulsifier, lubricant, binder, pH adjustor controller, isotonic agent and other conventional additives may be added.

The pharmaceutically acceptable or appropriate carrier may well include other compounds known to be beneficial to an impaired situation of the gut, (e.g., antioxidants, such as Vitamin C, Vitamin E, Selenium or Zinc); or a food composition. The food composition can be, but is not limited to, milk, yoghurt, curd, cheese, fermented milks, milk based fermented products, ice-creams, fermented cereal based products, milk based powders, infant formulae, tablets, liquid bacterial suspensions, dried oral supplement, or wet oral supplement.

An "extract" as used herein indicates either the insoluble material or soluble material obtained from the *B. fragilis* bacterial cell using various chemical, immunological, biochemical or physical procedures known to those of skill in the art, including but not limited to, precipitation, centrifugation, filtering, column chromatography, and detergent lysis. Extract can also cover PSA, the outer membrane vesicular and/or the supernatant fraction obtained from culturing the said *B. fragilis*.

The term "diluent" as used herein indicates a diluting agent which is issued to dilute or carry an active ingredient of a composition. Suitable diluent include any substance that can decrease the viscosity of a medicinal preparation.

In certain embodiments, compositions, compounds, and, in particular, pharmaceutical/extract/cell compositions can be formulated for enteral administration including, but not limited to, i) by mouth (orally) as tablets, capsules, or drops; ii) by gastric feeding tube, duodenal feeding tube, or gastrostomy; and enteral nutrition; and iii) rectally as a suppository.

In certain embodiments, the wild type *B. fragilis* cell, or extracts or PSA derived from the wild type, can be used as pharmaceuticals or food for the above enteral administration to treat or prevent inflammatory diseases, such as, but not limited to, inflammatory bowel disease (including Crohn's disease and ulcerative colitis), asthma, dermatitis, arthritis, myasthenia gravis, Grave's disease, multiple sclerosis, and psoriasis.

In some embodiments, the disclosed bacterial strain/cell, or OMVs derived from either the isolated (as disclosed) or wild type *B. fragilis*, can be used in a method of treating or preventing a condition in an individual.

The method comprises administering to the individual an effective amount of the composition or pharmaceutical/extract/cell/PSA composition comprising or derived from either the isolated *B. fragilis* strain (as disclosed here) or wild type *B. fragilis*; or a combination thereof. The term "individual" as used herein includes a single biological organism wherein inflammation can occur including but not limited to animals and in particular higher animals and in particular vertebrates such as mammals and in particular human beings.

The wild type *B. fragilis* or the isolated *B. fragilis* cell, or extracts, OMVs, or PSA derived from wild type or the isolated *B. fragilis* can be administered as part of or in the form of a nutritional composition, such as but not limited to a beverage, a drink, a bar, a snack, an ice cream, a dairy product, for example a chilled or a shelf-stable dairy product, a confectionery product, a cereal product such as a breakfast cereal, a frozen product intended for consumption after heating in a micro-wave or an oven, a ready-to-eat product, a fast food or a nutritional formula (which encompasses any nutritionally complete or supplementary formulation).

In alternative embodiments, the wild type *B. fragilis* or the isolated *B. fragilis* cell, or extracts, OMVs, or PSA derived from wild type *B. fragilis* or the isolated *B. fragilis*, can be administered as or part of a neutraceutical; a probiotic alone (or in combination with other probiotics); a pharmaceutical; a medicinal formulation, a cream, or a lotion.

The term neutraceutical, as used in this application, refers to a food, food product, fortified food or a dietary supplement that provides health and medical benefits, including the prevention and treatment of disease.

The "effective amount", "amount effective to," or "amount of X effective to" refers to an amount of the compound, composition or pharmaceutical/extract/cell composition that is effective to treat, relieve, reduce, or improve to some extent one or more of the symptoms of the disease in need of treatment, or to retard initiation of clinical markers or symptoms of a disease in need of prevention, when the compound is administered. Thus, for example an effective amount refers to an amount of the compound/composition/pharmaceutical ingredient which exhibits the 'improved' effects, as noted below.

The "effective amount" may be empirically determined by experimenting with the compounds concerned in known in vivo and in vitro model systems for a disease in need of treatment. An effective amount will vary according to the weight, sex, age and medical history of the individual, as well as the severity of the patient's condition(s), the type of disease(s), mode of administration, and the like. An effective amount may be readily determined using routine experimentation, e.g., by titration (administration of increasing dosages until an effective dosage is found) and/or by reference to amounts that were effective for prior patients. Generally, the effective amount of the present invention will be administered in dosages ranging between about 0.1 mg/kg and about 20 mg/kg of the patient's body-weight.

As used herein, the phrase "prophylactically effective amount" includes the amount of the compound/composition/pharmaceutical/extract/cell composition which is sufficient to result in the prevention or reduction of the development, recurrence or onset of one or more symptoms associated with a disorder (or to enhance or improve the prophylactic effect(s) of another therapy (e.g., another prophylactic agent).

It is further contemplated that the compound/composition/pharmaceutical/extract/cell composition of the present invention can be used with one or more known medicaments known to be useful in the treatment or prevention of inflammatory diseases, either separately or in combination.

For example the compound/composition/pharmaceutical/extract/cell composition of the present invention can be combined with one or a combination of medicaments/treatments known to be useful in the treatment of IBD such as, but not limited to, sulfasalazine (Azulfadine), mesalamine (Asacol, Pentasa), immunosuppressants (Imuran, 6-MP, cyclosporine); methotrexate, TNF-alpha inhibitors (Remicade and Humira); and corticosteroids (Entocort and prednisone). Other treatments (experimental) for ulcerative colitis, include aloe vera, butyrate, boswellia, probiotics, antibiotics, immunosuppressive therapy, and nicotine.

For example the compound/composition/pharmaceutical/extract/cell/PSA of the present invention can be combined with one or a combination of medicaments/treatments known to be useful in the treatment of MS such as, but not limited to, Avonex®, Betaseron®, and Copaxone®. Rebif®; Extavia® Novantrone® (mitoxantrone); Tysabri® (natalizumab), and Gilenya® (fingolimod). Other drugs include intravenous immunoglobulin (IVIg) therapy, methotrexate, azathioprine (Imuran®), and cyclophosphamide (Cytoxan®); corticosteroids; Cytoxan® (cyclophosphamide); Imuran® (azathioprine); methotrexate; plasma exchange; pulse Solu-Medrol® (IV methylprednisolone); prednisone; Decadron® (dexamethasone); Medrol® (oral methylprednisolone); Plasmapheresis (plasma exchange); intravenous immunoglobulin (IVIg) therapy.

Generation of PSA-Only Producing Mutant Strain ("Isolated *B. Fragilis*")

To create the *B. fragilis* mutant that produces PSA only from the repertoire of capsular polysaccharides (CPS), the *B. fragilis* NCTC9343ΔPSB mutant (2) was used as a parent strain from which every CPS biosynthesis locus (PSC-PSH) except for that of PSA was deleted one at a time. DNA segments upstream and downstream of the region to be deleted were PCR amplified by using primers listed in Table 1. A second round of PCR using primers 1 (forward primer of the left flank) and 4 (reverse primer of the right flank) with the 1:1 mix of the two PCR products as templates was performed to fuse the left and right flanking DNA fragments using the 18 bp overlapping region engineered into primers 2 (reverse primer of the left flank) and 3 (forward primer of the right flank). The fused PCR product was digested with BamHI and cloned into the BamHI site of the *Bacteroides* conjugal suicide vector pNJR6. The plasmid was introduce into *Escherichia coli* (*E. coli*.) and subsequently conjugally transferred into *B. fragilis* NCTC9343 and the cointegrates were selected by resistance to erythromycin encoded by pNJR6. The cointegrate strain was passaged in nonselective medium for 5-8 days and then plated on nonselective medium (BHIS). The resulting colonies were replica plated to BHIS containing erythromycin and the erythromycin-sensitive colonies were screened by PCR to distinguish wild-type revertants from strains with desired mutation (Table 2).

TABLE 1

Primers used to PCR amplify upstream and downstream flanking regions.

| Primer name | Sequence | 5' addition | Purpose |
| --- | --- | --- | --- |
| SEQ ID. NO. 1 PSC primer-1 | AAATGCGTTGCTTTTGCTTT | GT GGATCC (BamHI) | Delete PSC - left flank |
| SEQ ID. NO. 2 PSC primer-2 | TTCGAAATCGTTTTGCTTCA | AAACCATGG | Delete PSC - left flank |
| SEQ ID. NO. 3 PSC primer-3 | CCATGGTTTATGCTGGCTTT | GATTTCGAA | Delete PSC - right flank |
| SEQ ID. NO. 4 PSC primer-4 | AACACTACGCCTACCCGATG | TT GGATCC (BamHI) | Delete PSC - right flank |
| SEQ ID. NO. 5 PSD primer-1 | TACTGACCGAACCCACATCA | GT GGATCC (BamHI) | Delete PSD - left flank |
| SEQ ID. NO. 6 PSD primer-2 | CGATCCGATCTGTCATAGCA | TAGCCGGTT | Delete PSD - left flank |
| SEQ ID. NO. 7 PSD primer-3 | AACCGGCTAAAAATGGAAGG | ATCGGATCG | Delete PSD - right flank |
| SEQ ID. NO. 8 PSD primer-4 | ATCGGCACTCCAACAGACTT | TT GGATCC (BamHI) | Delete PSD - right flank |
| SEQ ID. NO. 9 PSE primer-1 | ACTTACGTTCAACGCCATCC | GT GGATCC (BamHI) | Delete PSE - left flank |
| SEQ ID. NO. 10 PSE primer-2 | GAGATTGCCTGGGTGAAAAA | CTTATGGAC | Delete PSE - left flank |
| SEQ ID. NO. 11 PSE primer-3 | GTCCATAAGCTTGACGCACA | GGCAATCTC | Delete PSE - right flank |
| SEQ ID. NO. 12 PSE primer-4 | CGTGCAGGTAATGTGATTGG | TT GGATCC (BamHI) | Delete PSE - right flank |
| SEQ ID. NO. 13 PSF primer-1 | TTTGTGAGCGTTTGCTCAAT | GT GGATCC (BamHI) | Delete PSF - left flank |
| SEQ ID. NO. 14 PSF primer-2 | CATCCTCCCATGCCTAAAGA | GCACCGCAC | Delete PSF - left flank |
| SEQ ID. NO. 15 PSF primer-3 | GTGCGGTGCTGGTTTTTAAT | GGGAGGATG | Delete PSF - right flank |
| SEQ ID. NO. 16 PSF primer-4 | CTATGCCAAGCGGAAAGAAG | TT GGATCC (BamHI) | Delete PSF - right flank |
| SEQ ID. NO. 17 PSG primer-1 | CCCTATTGGCCGGTTTTATT | GT GGATCC (BamHI) | Delete PSG - left flank |
| SEQ ID. NO. 18 PSG primer-2 | TTGGCTTTATCGTCCGTACC | TTGAAGTGG | Delete PSG - left flank |
| SEQ ID. NO. 19 PSG primer-3 | CCACTTCAACACCATTGACG | TAAAGCCAA | Delete PSG - right flank |

TABLE 1 -continued

Primers used to PCR amplify upstream and downstream flanking regions.

| Primer name | Sequence | 5' addition | Purpose |
|---|---|---|---|
| SEQ ID. NO. 20 PSG primer-4 | CCCCTCTCCAATATCAGCAA | TT GGATCC (BamHI) | Delete PSG - right flank |
| SEQ ID. NO. 21 PSH primer-1 | ATTCCCGCAAGTGCAGATAG | GT GGATCC (BamHI) | Delete PSH - left flank |
| SEQ ID. NO. 22 PSH primer-2 | TTTAAGCGACGTGGAGGTTT | TGGGACTGA | Delete PSH - left flank |
| SEQ ID. NO. 23 PSH primer-3 | TCAGTCCCACCCACACAGTA | TCGCTTAAA | Delete PSH - right flank |
| SEQ ID. NO. 24 PSH primer-4 | CACTTACAGCCGTGAGCTTG | TT GGATCC (BamHI) | Delete PSH - right flank |

TABLE 2

Primers used to distinguish between wild-type revertants and deletion mutant strains.

| Primer name | Sequence | Target | Product size |
|---|---|---|---|
| SEQ ID. NO. 25 PSA F | GCGCAAGCTTCTGGTTTAAG | PSA wild-type | 1191 bp |
| SEQ ID. NO. 26 PSA R | CTCCAAAGCCTTCACTTTCG | | |
| SEQ ID. NO. 27 delPSA F | GCTAAGACCGTTGCCAAAAT | PSA deletion mutant | 1333 bp |
| SEQ ID. NO. 28 delPSA R | ACCCGCAAAACAGAAATGAC | | |
| SEQ ID. NO. 29 PSB F | AAATGCGTTGCTTTTGCTTT | PSB wild-type | 1245 bp |
| SEQ ID. NO. 30 PSB R | TTCGAAATCGTTTTGCTTCA | | |
| SEQ ID. NO. 31 delPSB F | CATGGAGAAAACATCGTTGG | PSB deletion mutant | 802 bp |
| SEQ ID. NO. 32 delPSB R | CCCAATATCGTTCAGCCAAA | | |
| SEQ ID. NO. 33 C127 | GGAGGATGTTTGAATTGGTGG | PSC wild-type | 979 bp |
| SEQ ID. NO. 34 delPSC C | CCCGCTTAATGCCCTAAAAT | | |
| SEQ ID. NO. 35 C127 | GGAGGATGTTTGAATTGGTGG | PSC deletion mutant | 2825 bp |
| SEQ ID. NO. 36 C121 | TATCCTGATGTTCTGCTTTTCCG | | |
| SEQ ID. NO. 37 delPSD F | GTATCCCGACGTTACGAGGA | PSD wild-type | 881 bp |
| SEQ ID. NO. 38 delPSD C | CGAGGAATCTTGGCATTGAT | | |
| SEQ ID. NO. 39 delPSD F | GTATCCCGACGTTACGAGGA | PSD deletion mutant | 1037 bp |
| SEQ ID. NO. 40 delPSD R | CCATTTGGATAGGCGAGAAA | | |
| SEQ ID. NO. 41 delPSE C | CTGAAAGCGCATTTTCAACA | PSE wild-type | 940 bp |
| SEQ ID. NO. 42 delPSE R | TGCATTTCATGGAGGAACAA | | |
| SEQ ID. NO. 43 delPSE F | TTGATGGGGAATGAATGGTT | PSE deletion mutant | 1687 bp |
| SEQ ID. NO. 44 delPSE R | TGCATTTCATGGAGGAACAA | | |

TABLE 2 -continued

Primers used to distinguish between wild-type revertants and deletion mutant strains.

| Primer name | Sequence | Target | Product size |
|---|---|---|---|
| SEQ ID. NO. 45 delPSF F | GCCCATGTCAGATTTGCTTT | PSF wild-type | 958 bp |
| SEQ ID. NO. 46 delPSF C | TAGGCAAAATATCCGGCATC | | |
| SEQ ID. NO. 47 delPSF F | GCCCATGTCAGATTTGCTTT | PSF deletion mutant | 1281 bp |
| SEQ ID. NO. 48 delPSF R | ATGAATGAAGCCGAAAATCG | | |
| SEQ ID. NO. 49 delPSG F | AATGCCGGTTGTTTTGGTTA | PSG wild-type | 802 bp |
| SEQ ID. NO. 50 delPSG C | ACAGAACCTGCTCCCACTGT | | |
| SEQ ID. NO. 51 delPSG F | AATGCCGGTTGTTTTGGTTA | PSG deletion mutant | 930 bp |
| SEQ ID. NO. 52 delPSG R | CGGATCATAAAATCGGCAAC | | |
| SEQ ID. NO. 53 delPSH F | CGGGTAAAACTCTGCCCATA | PSH wild-type | 923 bp |
| SEQ ID. NO. 54 delPSH C | GCTCGTATGGATGCTGATGA | | |
| SEQ ID. NO. 55 delPSH F | CGGGTAAAACTCTGCCCATA | PSH deletion mutant | 829 bp |
| SEQ ID. NO. 56 delPSH R | AGGTGCTTTCGTGATTGCTT | | |

We determined whether PSA could be detected in the outer membrane vesicles (OMV) extracts of our strain. For this purpose outer membrane vesicles (OMV) extracts were prepared based on a modification of a previously described protocol for the preparation of OMVs from E. coli (Amanda L. Horstman and Meta J. Kuehn. (2000) Enterotoxigenic Escherichia coli secretes active heat-labile enterotoxin via outer membrane vesicles. J Biol Chem. 275: 12489-12496.) Briefly, electron dense layer (EDL)-enriched B. fragilis was grown in customized MM. OMVs were recovered from the bacteria-free supernatant of the culture by centrifugation at 40,000 g for 2 hrs at 4 C and further washed twice with PBS and filtered through 0.45 μm spin columns (Millipore #20-218). Total protein concentration of the purified OMVs was determined by Bradford assay (Biorad #500-0205). FITC-labeled OMVs were prepared as previously described (Nicole C. Kesty and Meta J. Keuhn. (2004) Incorporation of heterologous outer membrane and periplasmic proteins into Escherichia coli outer membrane vesicles. J Biol Chem. 279: 2069-2076). Briefly, OMVs were incubated in the staining buffer (1 mg/ml FITC (Thermo Scientific #46424), 100 mM NaCl, 50 mM Na2CO3, pH 9.2) for 1 hr at RT. Labeled OMVs were collected by centrifugation at 40,000 g for 30 min at 4 C and washed twice with PBS+200 mM NaCl.

Figure 4:
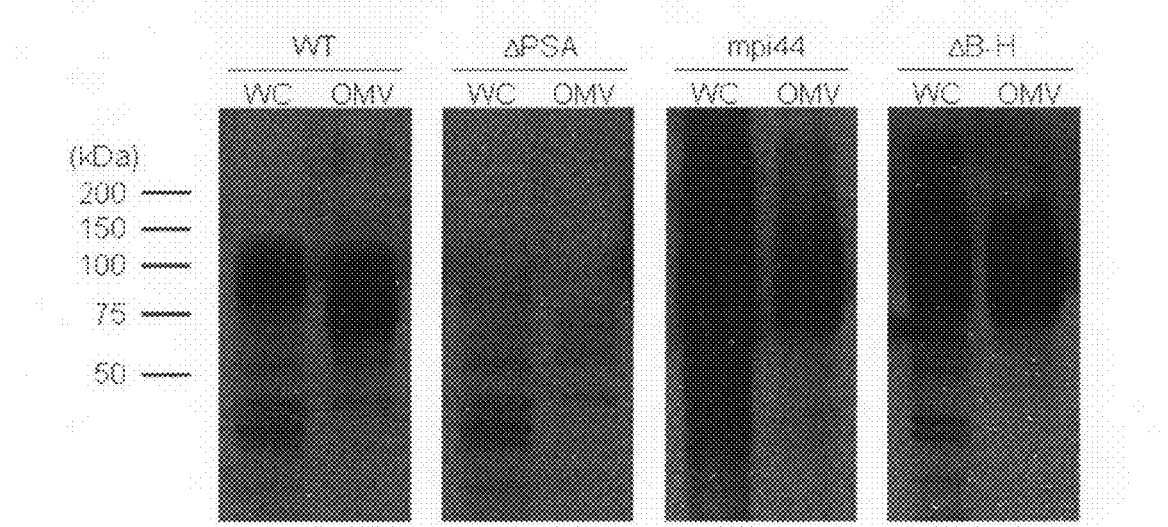
FIG. 4 shows an immunoblot analysis with PSA antiserum of whole cell (WC) and outer membrane vesicles (OMV) extracts from wild-type, PSA deletion mutant, Mpi deletion mutant expressing PSA only, and PSB through PSH deletion mutant *B. fragilis* show that all three PSA producing *B. fragilis* strains express PSA both on bacterial surface and with OMV. PSA-deletion mutant confirms specificity of the PSA antiserum.

FIG. 4 shows an immunoblot analysis for PSA production by whole cell lysates and OMVs. There are 4 bacterial strains analyzed: wild-type bacteria (positive control), PSA mutant (ΔPSA; negative control for antibody specificity), mpi44 (the previously used PSA production strain) and ΔB-H (the newly created strain in this application). As can be seen, PSA is produced as expected in the ΔB-H strain in both the whole cell and outer membrane vesicles (OMV) extracts; the latter confirming that PSA is actively sorted into the OMVs of our strain.

The disclosed bacterial strain/cell can be used to treat or prevent a variety of diseases, such as but not limited to, inflammatory bowel disease, Crohn's disease and ulcerative colitis, asthma, dermatitis, arthritis, myasthenia gravis, Grave's disease, multiple sclerosis (MS), type I diabetes, type 2 diabetes, food allergy, and psoriasis. Thus, either the live, viable or lyophilized embodiments of the bacteria cell disclosed expresses only PSA can be administered alone or part of a pharmaceutical; or in conjunction with any other therapeutic agent useful in the treatment the aforementioned diseases. In another embodiments, the OMVs from the disclosed bacterial strain/cell can be can be administered alone or part of a pharmaceutical; or in conjunction with any other therapeutic agent useful in the treatment the aforementioned diseases.

It should be mentioned that prior investigators have described an isolated Bacteroides fragilis bacterial cell producing a native capsular polysaccharide A (PSA), having a native promoter that controls expression of native biosynthetic genes of PSA and native promoters that control expression of native biosynthetic genes of native capsular polysaccharides PSB, PSD, PSE, PSF, PSG and PSH, wherein the promoter that controls expression of the native biosynthetic genes of PSA is locked on, wherein at least one of the promoters that controls expression of the native biosynthetic genes of the native capsular polysaccharides selected from the group consisting of: PSB, PSD, PSE, PSF, PSG, and PSH is locked off, wherein the promoter controlling expression of the native biosynthetic genes of PSA is locked on by deletion of the gene that encodes for a DNA recombinase that inverts promoters. Upon deletion of this gene, named multiple promoter invertase (mpi), bacterial isolates were screened for a strain that has the PSA promoter in the locked on orientation, but all other promoters in the locked off orientation. In that study, the promoter controlling expression of a capsular polysaccharide is "locked on" when the invertible promoter is in its transcriptionally active orientation and it cannot invert to the transcriptionally inactive orientation. The promoter can be locked on because a sequence-specific enzyme that normally inverts the promoter is not present or is otherwise disabled. Alternatively, the promoter can be locked on because at least one inverted repeat flanking the invertible region of the promoter is altered, e.g., deleted, so that the inversion is not possible. Alternatively, the promoter controlling expression of a capsular polysaccharide is "locked off" when the invertible promoter is in its transcriptionally inactive orientation and it cannot invert to the transcriptionally active orientation. The promoter can be locked off because a sequence-specific enzyme that normally inverts the promoter is not present or is otherwise disabled. Alternatively, the promoter can be locked off because at least one inverted repeat flanking the invertible region of the promoter is altered, e.g., deleted, so that the inversion is not possible.

Figure 5:
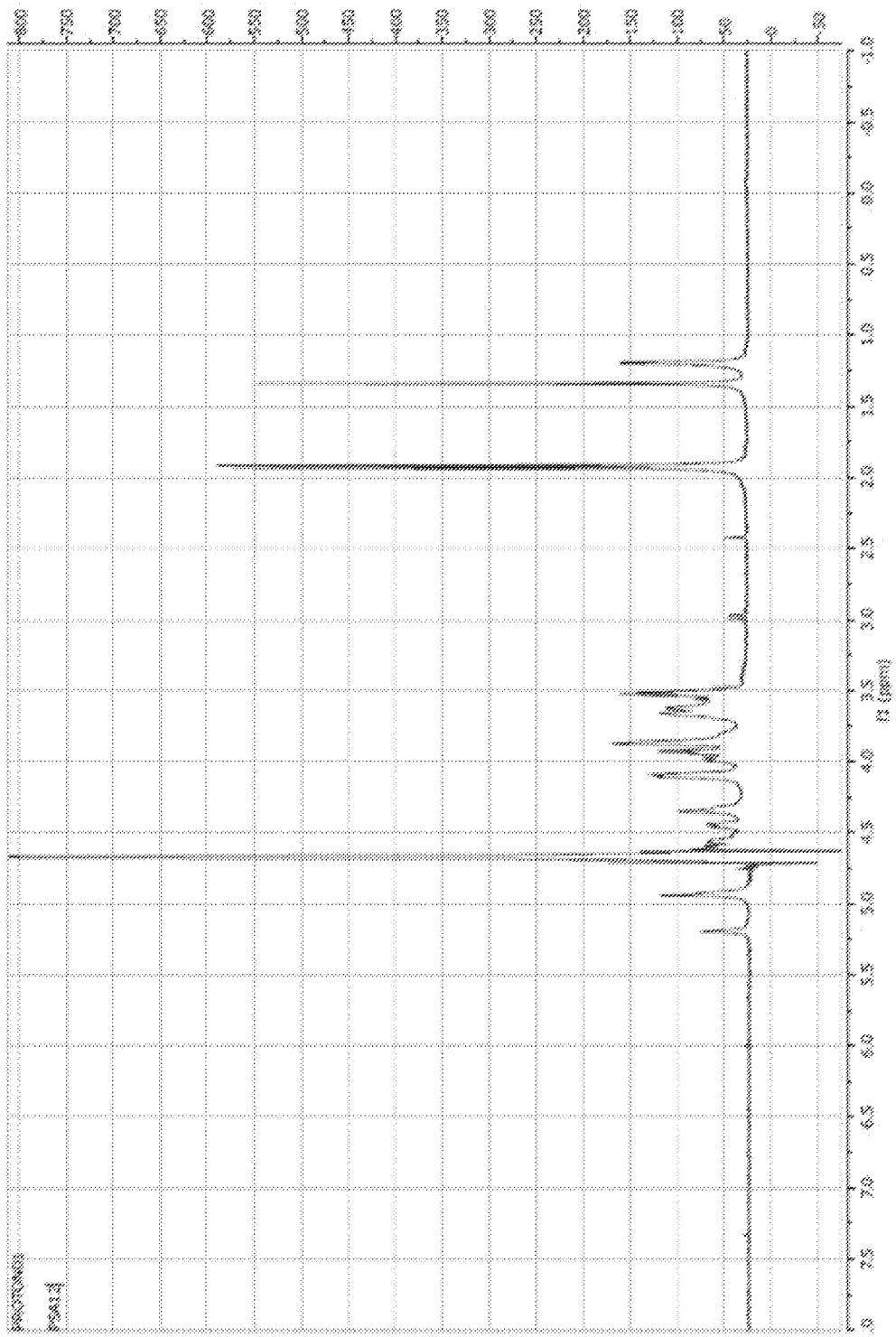
FIG. 5 shows a NMR spectra for PSA (PSA12) from a PSA-only expressing mutant (*B. fragilis*ΔPSB-PSH) bacteria.

FIG. 5 shows that the PSA-only expressing mutant (*B. fragilis*ΔPSB-PSH) bacteria serves its purpose to facilitate purification of PSA as evidenced by NMR.

Figure 6:
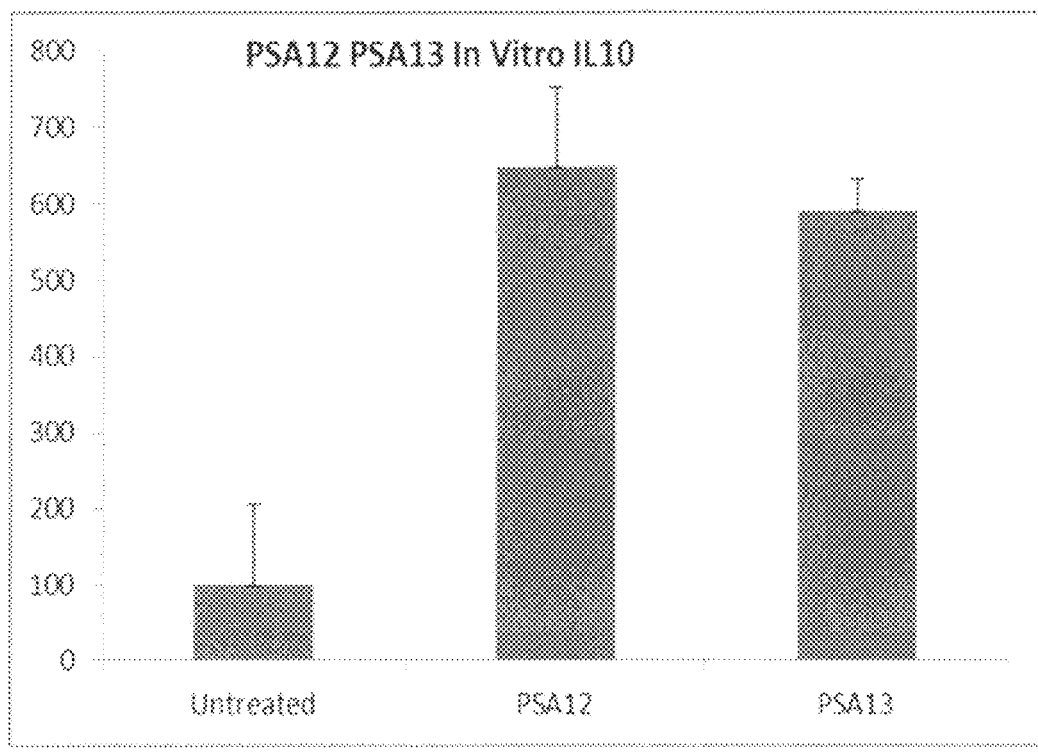
FIG. 6 shows induction of IL-10 from in vitro cultures of dendritic cells and T cells treated with purified PSA (PSA12 and PSA 13) from a PSA-only expressing mutant (*B. fragilis*-ΔPSB-PSH) bacteria.

FIG. 6 shows the induction of IL-10 from in vitro cultures of dendritic cells and T cells treated with PSA purified from the A-only expressing mutant (*B. fragilis*ΔPSB-PSH) bacteria (PSA12 and PSA13). Both PSAs look similar.

REFERENCES (WHICH ARE ALL INCORPORATED BY REFERENCE IN THEIR ENTIRETY)

1. Liu C H, Lee S M, Vanlare J M, Kasper D L, Mazmanian S K. 2008. Regulation of surface architecture by symbiotic bacteria mediates host colonization. *Proc Natl Acad Sci USA* 105: 3951-6
2. Coyne M J, Kalka-Moll W, Tzianabos A O, Kasper D L, Comstock L E. 2000. *Bacteroides fragilis* NCTC9343 produces at least three distinct capsular polysaccharides: cloning, characterization, and reassignment of polysaccharide B and C biosynthesis loci. *Infect Immun* 68: 6176-81

The invention claimed is:

1. A recombinant *Bacteroides fragilis* (*B. fragilis*) bacterial cell expressing a native capsular polysaccharide A (PSA), and lacking expression of native capsular polysaccharide B (PSB), capsular polysaccharide C (PSC), capsular polysaccharide D (PSD), capsular polysaccharide E (PSE), capsular polysaccharide F (PSF), capsular polysaccharide G (PSG), and capsular polysaccharide H (PSH), wherein biosynthetic genes for native capsular polysaccharides PSB, PSC, PSD, PSE, PSF, PSG, and PSH are deleted from the cell's genome, and wherein a native multiple promoter invertase (mpi) gene that controls expression of native biosynthetic genes of native capsular polysaccharides PSA, PSB, PSD, PSE, PSF, PSG and PSH has not been mutated or deleted.

2. The cell of claim 1, wherein the PSA is present on outer membrane vesicles produced by the cell.

3. The cell of claim 1, wherein the cell is administered, as part of a pharmaceutical, to an individual suffering from an inflammatory disease or condition.

4. The cell of claim 2, wherein the outer membrane vesicles are administered, as part of a pharmaceutical, to an individual suffering from an inflammatory disease or condition.

5. A method of treating inflammatory bowel disease comprising administering to a subject in need thereof an effective amount of a pharmaceutical composition comprising the recombinant *B. fragilis* according to claim 1.

* * * * *